United States Patent
Shibata

(10) Patent No.: US 8,650,838 B2
(45) Date of Patent: Feb. 18, 2014

(54) DRUG DELIVERY DEVICE AND DRUG DELIVERY METHOD

(75) Inventor: Shoji Shibata, Ehime (JP)

(73) Assignee: Panasonic Corporation, Osaka (JP)

( * ) Notice: Subject to any disclaimer, the term of this patent is extended or adjusted under 35 U.S.C. 154(b) by 325 days.

(21) Appl. No.: 13/119,354

(22) PCT Filed: Sep. 14, 2009

(86) PCT No.: PCT/JP2009/004578
§ 371 (c)(1),
(2), (4) Date: Mar. 16, 2011

(87) PCT Pub. No.: WO2010/032426
PCT Pub. Date: Mar. 25, 2010

(65) Prior Publication Data
US 2011/0162323 A1    Jul. 7, 2011

(30) Foreign Application Priority Data

Sep. 19, 2008  (JP) ................................ 2008-241836

(51) Int. Cl.
*B65B 61/26*  (2006.01)
(52) U.S. Cl.
USPC ............................ 53/411; 53/135.1; 53/136.4
(58) Field of Classification Search
USPC ............... 53/411, 135.1, 136.1, 136.4, 131.4; 700/236, 242, 244
See application file for complete search history.

(56) References Cited

U.S. PATENT DOCUMENTS 5,604,692 A * 2/1997 Yuyama ........................ 708/714
5,988,858 A * 11/1999 Yuyama et al. ............... 700/230
6,181,979 B1 * 1/2001 Murakami ..................... 700/216
6,701,218 B2 * 3/2004 Koike et al. ................... 700/235
7,912,578 B1 * 3/2011 Frankel ......................... 700/237

(Continued)

FOREIGN PATENT DOCUMENTS

JP    6-127184    5/1994
JP    9-51922     2/1997

(Continued)

OTHER PUBLICATIONS

International Search Report issued Dec. 28, 2009 in International (PCT) Application No. PCT/JP2009/004578.

*Primary Examiner* — Hemant M Desai
(74) *Attorney, Agent, or Firm* — Wenderoth, Lind & Ponack, L.L.P.

(57) ABSTRACT

A drug delivery device (1) delivers a stored drug to a conveyance receptacle (T) adapted to be attached with a card (RC) that displays desired information. The drug delivery device (1) includes a transportation unit (P), a card supply unit (70), a card attachment unit (20), and a card preparation unit (50). The transportation unit (P) transports plural conveyance receptacles in a sequential manner. The card supply unit (70) supplies a first card (RC1) to be attached to a first conveyance receptacle (T1) that is first transported among the plural conveyance receptacles (T). The card attachment unit (20) takes out second cards (RC2) from the respective plural conveyance receptacles (T) and attach the taken out second cards to second conveyance receptacles (T2) that are transported after the first conveyance receptacle (T1) respectively. The card preparation unit (50) prepares the first card (RC1) and the second cards (RC2) so as to display patient identification information thereon. With the drug delivery device (1), it is possible to reduce the waiting time of the trays (T).

9 Claims, 13 Drawing Sheets

(56) References Cited

U.S. PATENT DOCUMENTS

| | | | |
|---|---|---|---|
| 8,091,213 B2 * | 1/2012 | Yuyama et al. | 29/701 |
| RE43,549 E * | 7/2012 | Koike et al. | 700/235 |
| 2002/0063698 A1 * | 5/2002 | Koike et al. | 345/173 |
| 2004/0123564 A1 * | 7/2004 | McErlean et al. | 53/411 |

FOREIGN PATENT DOCUMENTS

| | | |
|---|---|---|
| JP | 2005-161736 | 6/2005 |
| JP | 2005-279268 | 10/2005 |
| JP | 3737697 | 11/2005 |
| JP | 2006-109900 | 4/2006 |

* cited by examiner

US 8,650,838 B2

DRUG DELIVERY DEVICE AND DRUG DELIVERY METHOD

TECHNICAL FIELD

The present invention relates to a drug delivery device and a drug delivery method for delivering a drug stored in a cassette or the like to a conveyance receptacle.

BACKGROUND ART

There are conventional drug delivery devices with which ampoules, vials, plastic bottles, kits, bags, or the like containing a drug or the like are pre-loaded into a cassette and then delivered as needed.

FIG. 12 is an overall view of the configuration of a conventional drug delivery device 100 (see Patent Citation 1, for example).

The drug delivery device 100 has cassettes 102 containing a drug 104, a shelf 103 for holding the cassettes, and a device 105 for delivering the drug. The shelf 103 is divided laterally and longitudinally into numerous compartments, forming a plurality of cells 123. Each of the cells 123 holds a cassette 102 filled with the drug 104. A single cassette 102 is filled with several dozen (for example) units of the same type of drug 104.

The device 105 has an extractor 106 for extracting a drug from the cassette 102. The extractor 106 is controlled by a specific control device, and moves in the directions of the arrows 12A and 13A in the drawing. The extractor 106 is positioned on a rear face 3B of the holding shelf with respect to the cassette 102 containing the desired drug 104. The extractor 106 has a unit similar to a known robot arm (not shown). The robot arm takes the drug 104 out of the cassette 102 and delivers it to a delivery tray 141.

The delivery tray 141 is divided into a plurality of regions by partition plates 142. The drug that is to be delivered is delivered to each region according to drug administration zones. The delivery tray 141 by which the drug 104 is delivered is transported to the drug administration site, such as a hospital ward.

As discussed above, with a conventional drug delivery device, ampoules or the like of drug are stored in trays (conveyance receptacles) for each patient and transported to each patient. Therefore, each tray must display information that identifies the corresponding patient. This is so that the stored drug or the like will be handed to the correct patient, or used on the correct patient.

One display means for identifying the trays (conveyance receptacles) is a display label. The display label is a label having a label paper or a self-adhesive label with patient identification information or the like printed on. The display label is attached by hand to one side of a tray, and is removed by hand when the tray is no longer needed. However, the attachment and removal of the display labels and so forth can entail a great deal of work, and for this and other reasons, the use of rewritable cards that can be written to repeatedly is known (see Patent Citation 2, for example).

FIG. 13 shows a conventional drug delivery device 200 with which cards (display members) are automatically and removably attached to trays.

The drug delivery device 200 has a card attachment and removal conveyance means 210 and a writing means 220. The card attachment and removal conveyance means 210 conveys a rewritable card 201, which is attached to or removed from a tray T, between the tray T and the writing means 220. The writing means 220 writes patient identification information on the rewritable card 201. The writing means 220 is connected to the card attachment and removal conveyance means 210.

With the drug delivery device 200 above, when a tray T that has been transported in comes to a stop, the rewritable card 201 attached to that tray is removed by the card attachment and removal conveyance means 210. The removed rewritable card 201 is sent between plastic rollers and rubber rollers 212 of the card attachment and removal conveyance means 210, and conveyed to the writing means 220. The conveyed rewritable card 201 is printed by the writing means 220, sent back along the rubber rollers 212 and the plastic rollers, and attached to the tray T by the card attachment and removal conveyance means 210.

PRIOR ART PUBLICATIONS

Patent Citations

Patent Citation 1: Japanese Laid-Open Patent Application 2006-109900

Patent Citation 2: Japanese Laid-Open Patent Application 2005-279268

DISCLOSURE OF INVENTION

Technical Problem

With the card attachment and removal unit of the above-mentioned drug delivery device, each tray T is transported while having thereon a rewritable card 201 before being printed, and then stopped in front of the card attachment and removal conveyance means 210. The card attachment and removal conveyance means 210 removes the rewritable card 201 from the tray T and feeds the rewritable card to the writing means 220. The rewritable card 201 is printed by the writing means 220 and then fed back to the card attachment and removal conveyance means 210, where the card is attached to the stopped tray T.

With the above-mentioned drug delivery device, transported trays T need to wait in front of the card attachment and removal conveyance mean 210 until rewritable cards 201 are printed and fed back to the card attachment and removal conveyance mean 210. Therefore, trays T have to be stopped for a long time, which reduces the efficiency of transporting trays T. This results in low drug delivery efficiency of the device.

It is an object of the present invention to provide a drug delivery device and a drug delivery method with which the waiting time of trays is shortened, and the efficiency of drug delivery can be improved.

Technical Solution

The drug delivery device pertaining to a first aspect of the invention is a drug delivery device that delivers a stored drug to a conveyance receptacle adapted to be attached with a card that displays desired information, said drug delivery device comprising a transportation unit, a card supply unit, a card attachment unit, and a card preparation unit. The transportation unit is configured to transport plural conveyance receptacles in a sequential manner. The card supply unit is configured to supply a first card to be attached to a first conveyance receptacle that is first transported among the plural conveyance receptacles. The card attachment unit is configured to take out second cards from the respective plural conveyance receptacles and attach the taken out second cards to second conveyance receptacles that are transported after the first conveyance receptacle respectively. The card preparation unit is configured to prepare the first and second cards so as to display patient identification information thereon.

With the above drug delivery device, a card is taken out from the first conveyance receptacle that is first transported and specific information is written on that card, while specific information is written on a first card that is supplied by the card supply unit and the first card is attached to the first conveyance receptacle. With respect to the second conveyance receptacles that are transported after the first conveyance receptacle, second cards are respectively taken out from conveyance receptacles that are transported previous to the respective second conveyance receptacles, written with information, and then attached to the second conveyance receptacles respectively.

The "drug" referred to here is a drug that can be prescribed, such as an injection drug, an oral drug, an ointment, a plaster, a suppository, or the like. Examples of the "patient identification information" include the patient's name, ID number, sex, date of birth, department name, hospital ward name, and room number.

The card supply unit may be, for example, a card holder that is capable of holding plural cards. The card supply unit may be a card holding portion of the card attachment unit or the card preparation unit and holds a first card in the card holding portion.

The second conveyance receptacles include all conveyance receptacles that are transported after the first conveyance receptacle that is first transported. The second cards include a card attached to the first conveyance receptacle and all cards attached to the second conveyance receptacles that are transported after the first conveyance receptacle.

With such structures, the first card to be attached to the first conveyance receptacle that is first transported is written with specific information and prepared by the time the first conveyance receptacle is transported. Therefore, it is possible to efficiently attach the first card to the first conveyance receptacle that is first transported. Furthermore, with respect to the second conveyance receptacle that is transported next, a second card that has been taken out from the first conveyance receptacle is written with specific information and prepared by the time the second conveyance receptacle is transported. Therefore, it is also possible to efficiently attach the second card. Similarly, with respect to the subsequent conveyance receptacles (second receptacles), it is possible to efficiently attach the cards that have been taken out from the previously transported second conveyance receptacles. As a result, the waiting time of the conveyance receptacles for attachment of cards is reduced and the efficiency of transporting the conveyance receptacles is enhanced. Consequently, the efficiency of drug delivery will be improved.

In this context, the conveyance receptacle to which the card attachment unit attaches a second card is not limited to a conveyance receptacle that is transported subsequent to the one from which the second card has been taken out. It may be the one transported right after the subsequent one from which the second card has been taken out, or even any conveyance receptacle transported as a further subsequent one. When a second card is to be attached after being taken out can be determined flexibly in accordance with a card preparation time taken by the card preparation unit or a transportation speed of the conveyance receptacles.

The drug delivery device pertaining to a second aspect of the invention is the drug delivery device pertaining to the first aspect, wherein the card attachment unit attaches the first card to the first conveyance receptacle substantially simultaneously with taking out the second card from the first conveyance receptacle and conveying the second card to the card preparation unit. The card attachment unit further attaches previously obtained second cards to the second conveyance receptacles respectively, substantially simultaneously with taking out new second cards from the second conveyance receptacles and conveying the new second cards to the card preparation unit respectively.

With the drug delivery device, the next card (second card) is taken out from the first conveyance receptacle that is first transported and goes through the card preparation process, and at the same time, a card (first card) is attached to the first conveyance receptacle. Similarly, another next card (other second card) is taken out from a second conveyance receptacle that is transported subsequent to the first conveyance receptacle, and at the same time, the card that has been prepared is attached to that second conveyance receptacle.

This enables the cards to be attached efficiently and reliably.

The drug delivery device pertaining to a third aspect of the invention is the drug delivery device pertaining to the first aspect, wherein the first and second cards are rewritable cards.

The "rewritable card" referred to here is a card that can be rewritten. Examples of rewritable card include leuco cards that change color when a leuco dye in the recording layer reacts and bonds with a developer, and what are known as light-scattering rewritable cards. For instance, with a leuco rewritable card, information can be rewritten by taking advantage of the properties of coloration (bonding of the dye and the developer) by high-temperature heating and rapid cooling, and erasure (separation of the dye and the developer) by low-temperature heating and gradual cooling.

A rewritable card that allows the card to be rewritten is utilized here. Consequently, a card that has been inserted in the conveyance receptacle can be used again while still attached to the conveyance receptacle during the next time a drug is delivered, which eliminates the trouble of having to reinsert a new card, etc.

The drug delivery device pertaining to a fourth aspect of the invention is the drug delivery device pertaining to the first aspect, wherein the card supply unit is a card holder configured to hold extra cards, and the card preparation unit obtains the first card from the card holder.

For the device, the card holder as a card supplier for supplying new cards is provided. This enables a card (first card) to be prepared ahead of time for the conveyance receptacle that is first transported. Consequently, it is possible to reduce the waiting time of the conveyance receptacles.

The drug delivery device pertaining to a fifth aspect of the invention is the drug delivery device pertaining to the fourth aspect, wherein the card preparation unit obtains the second card from the card holder when the card preparation unit is not able to obtain the second card from the first or second conveyance receptacle.

With the drug delivery device, the second card is supplied from the card holder in such a abnormal case that a new card could not be obtained. Examples of the abnormal case include a case where a new card could not be obtained from a conveyance receptacle, a case where the unit fails to take out a new card, and the like. In such cases, a selection is made to supply a card from the card supply unit.

Consequently, it is possible to backlog a supply source for new cards, thus preventing a shortage of cards.

The drug delivery method pertaining to a sixth aspect of the invention is a drug delivery method of delivering a stored drug to a conveyance receptacle adapted to be attached with a card that displays desired information, said drug delivery method comprising a transportation step, a supply step, an attachment step, and a card preparation step. In the transportation step, plural conveyance receptacles are transported in a sequential manner. In the supply step, a first card, which is to be attached to a first conveyance receptacle that is first transported among the plural conveyance receptacles, is supplied. In the attachment step, second cards are taken out from the respective plural conveyance receptacles and attached to second conveyance receptacles that are transported after the first conveyance receptacle. In the card preparation step, patient identification information is displayed on the first and second cards respectively.

With the above method, the first card to be attached to the first conveyance receptacle that is first transported is written with specific information and prepared by the time the first conveyance receptacle is transported. Therefore, it is possible to efficiently attach the first card to the first conveyance receptacle that is first transported. Furthermore, with respect to the second conveyance receptacle that is transported next, for example, a second card that has been taken out from the first conveyance receptacle is written with specific information and prepared by the time the second conveyance receptacle is transported. Therefore, it is also possible to efficiently attach the second card. Similarly, with respect to the subsequent conveyance receptacles (second receptacles), it is possible to efficiently attach the cards that have been taken out from the previously transported second conveyance receptacles. As a result, the waiting time of the conveyance receptacles for attachment of cards is reduced and the efficiency of transporting the conveyance receptacles is enhanced. Consequently, the efficiency of drug delivery will be improved.

The drug delivery device pertaining to a seventh aspect of the invention is the drug delivery device pertaining to the second aspect, wherein the first and second cards are rewritable cards.

A rewritable card that allows the card to be rewritten is utilized here. Consequently, a card that has been inserted in the conveyance receptacle can be used again while still attached to the conveyance receptacle during the next time a drug is delivered, which eliminates the trouble of having to reinsert a new card, etc.

The drug delivery device pertaining to an eighth aspect of the invention is the drug delivery device pertaining to the second aspect, wherein the card supply unit is a card holder configured to hold extra cards, and the card preparation unit obtains the first card from the card holder.

For the device, the card holder as a card supplier for supplying new cards is provided. This enables a card (first card) to be prepared ahead of time for the conveyance receptacle that is first transported. Consequently, it is possible to reduce the waiting time of the conveyance receptacles.

The drug delivery device pertaining to a ninth aspect of the invention is the drug delivery device pertaining to the third aspect, wherein the card supply unit is a card holder configured to hold extra cards, and the card preparation unit obtains the first card from the card holder.

For the device, the card holder as a card supplier for supplying new cards is provided. This enables a card (first card) to be prepared ahead of time for the conveyance receptacle that is first transported. Consequently, it is possible to reduce the waiting time of the conveyance receptacles.

Advantageous Effects

With the drug delivery device and drug delivery method pertaining to the present invention, the waiting time of conveyance receptacles is reduced, and therefore the efficiency of drug delivery is improved.

MODE FOR CARRYING OUT THE INVENTION

1. First Embodiment

The drug delivery device 1 pertaining to an embodiment of the present invention will be described through reference to FIGS. 1 to 11.

In the following description, the term "drug" is a drug that can be prescribed, such as an injection drug, an oral drug, an ointment, a plaster, a suppository, or the like.

1.1. Overall Configuration of Drug Delivery Device 1

Figure 1:
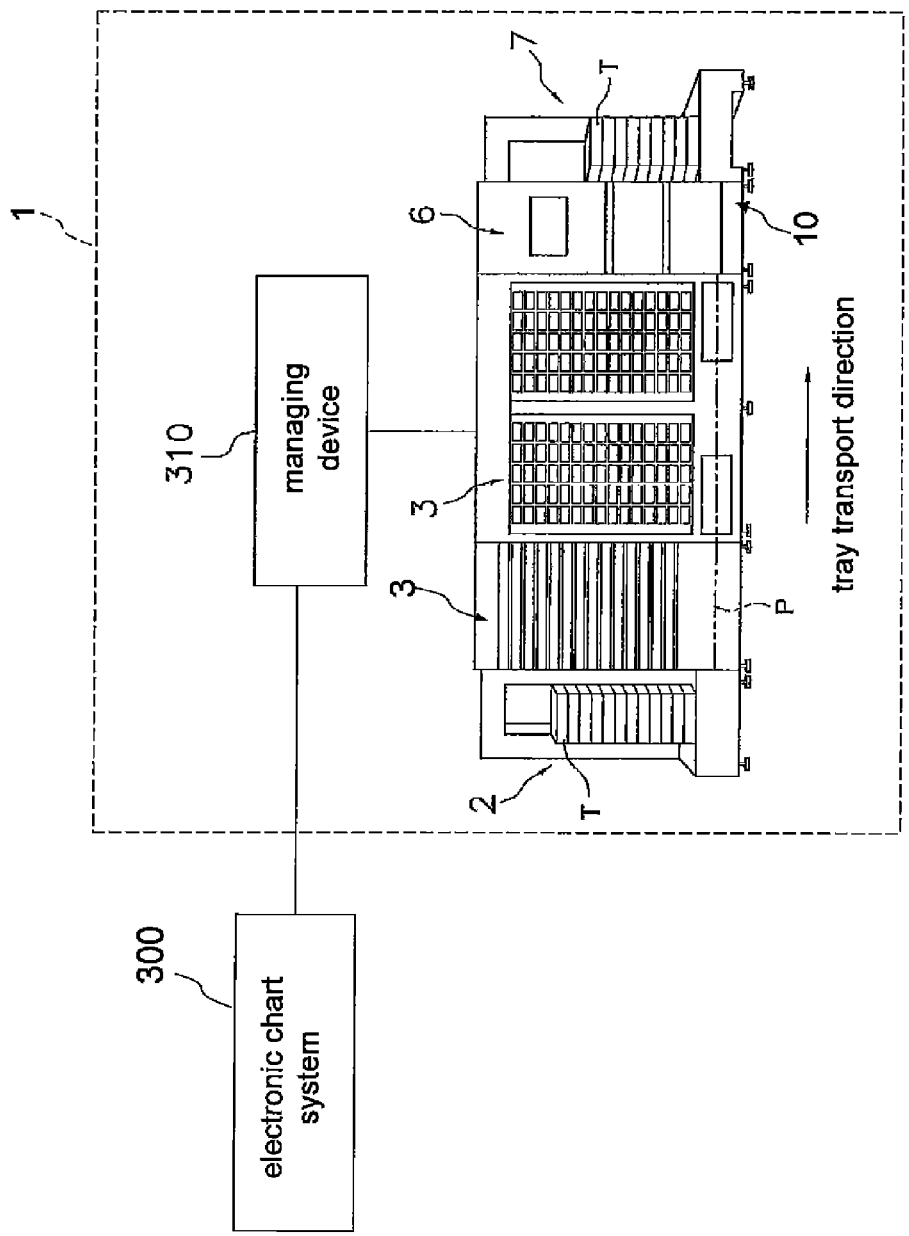
FIG. 1 is an overall view of the drug delivery device pertaining to an embodiment.

FIG. 1 shows an overall view of the drug delivery device 1 pertaining to this embodiment.

Figure 2:
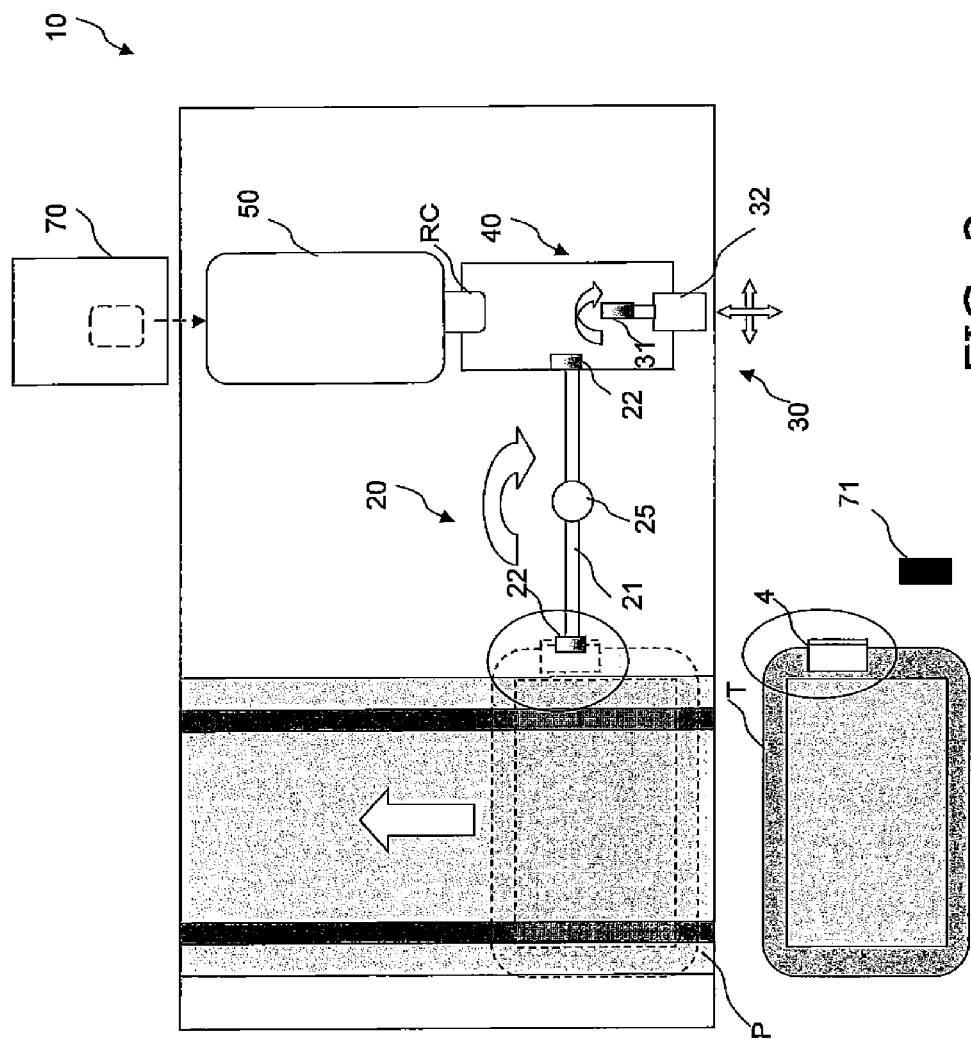
FIG. 2 is a top view of the card processing unit pertaining to this embodiment.

The drug delivery device 1 performs drug delivery processing according to patient identification information, drug administration information, prescription information, and so forth. Also, as shown in FIG. 2, the drug delivery device 1 recovers an unwritten rewritable card RC (hereinafter referred to as "unprinted rewritable card RC") from each tray (conveyance receptacle) T that is transported in, and at the same time automatically attaches a written rewritable card RC (hereinafter referred to as "printed rewritable card RC") with a card processing unit 10 (FIG. 2) to each tray T.

Various patient identification information and prescription information are sent from an electronic chart system 300 to a server or other such managing device 310. Examples of patient identification information include the patient's name, ID number, sex, date of birth, department name, hospital ward name, and room number, and this information is displayed on a rewritable card RC, a tray label, a drug administration label, a prescription, or the like. The drug administration information is the name of the drug to be administered to a patient, the amount of the drug, the administration date and time, and so forth, and this information is displayed mainly on the drug administration label. Prescription information is the details of what is written on the prescription, and includes patient identification information as well as the name of the prescribed drug, its dosage, the administration date and time, the amount to be taken each time, the administration method, and so forth. These different kinds of information are not strictly categorized, and there may be some overlap in all or part of the information.

The patient identification information, drug administration information, prescription information, and so forth are sent form the electronic chart system 300 to the managing device 310.

The trays T that are transported are A4 or A3-size holders. An unprinted rewritable card RC is attached to a card pocket 4 (FIG. 3) as discussed below for each tray T prior to transport.

Figure 3:
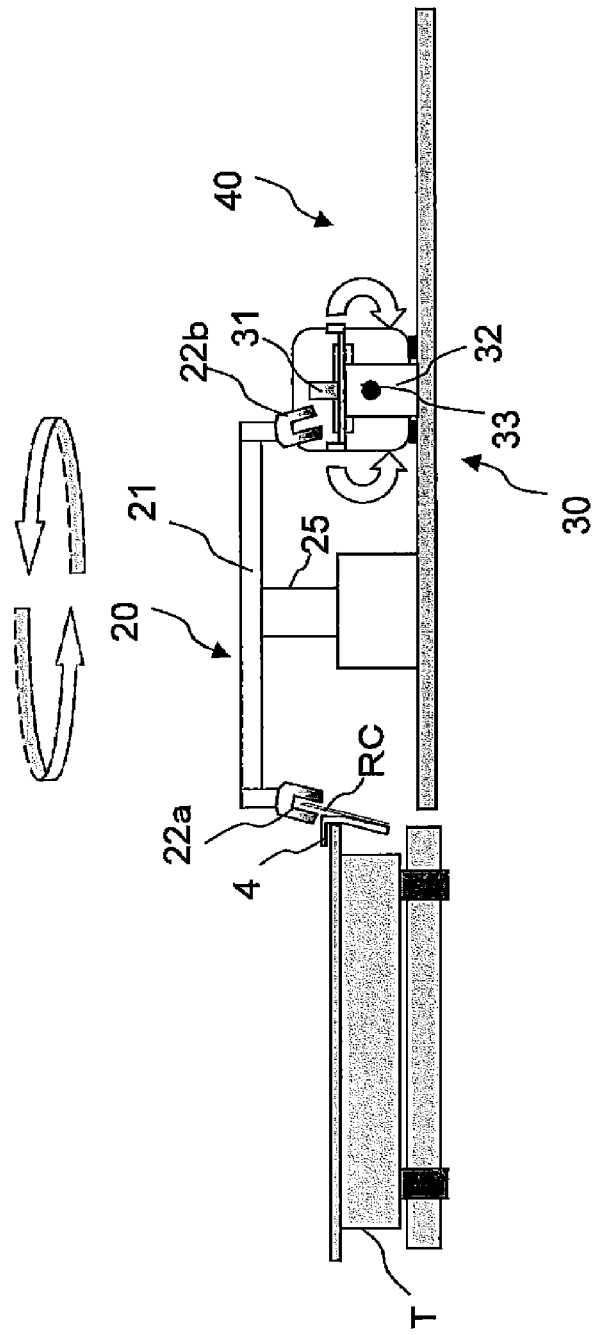
FIG. 3 is a front view of the card processing unit pertaining to this embodiment.

As shown in FIG. 3, the card pocket 4 is attached at one end on the card processing unit 10 side of the tray T. As also shown in FIG. 3, the card pocket 4 is formed so that its upper part is inclined to the card processing unit 10 side with respect to the vertical face of the tray T. The card pocket 4 is open at the top, and a rewritable card RC is inserted into this opening. The card pocket 4 is also open on the sides, so the rewritable card RC may instead be inserted from the side.

The rewritable card RC is a card that can be rewritten. Examples of rewritable card include leuco cards that change color when a leuco dye in the recording layer reacts and bonds with a developer, and what are known as light-scattering rewritable cards. For instance, with a leuco rewritable card, information can be rewritten by taking advantage of the properties of coloration (bonding of the dye and the developer) by high-temperature heating and rapid cooling, and erasure (separation of the dye and the developer) by low-temperature heating and gradual cooling. However, some other card-shaped object with which a display can be changed can be used instead of a rewritable card. What is mainly printed on the rewritable card RC is patient identification information.

This drug delivery device 1 primarily comprises a tray supply unit 2, a drug delivery unit 3, a tray transport path P, a label/prescription printing unit 6 (FIG. 7), a completed tray stacking unit 7, and a card processing unit 10. The drug delivery device 1 also comprises a device controller 5 and a managing device 310 (FIG. 8) as controllers, which control the various units.

The tray supply unit 2 sends out the stacked trays T one at a time into the tray transport path P at a command from the device controller 5 of the drug delivery device 1. The trays T are transported in the direction of the arrow in FIG. 1 along the tray transport path P, and temporarily come to a stop at a specific position near the drug delivery unit 3.

The drug delivery unit 3 is disposed opposite the tray transport path P and downstream from the tray supply unit 2. The drug delivery unit 3 has a drug holding means such as cassettes or drawers for holding drugs, and a pickup means for automatically taking the drugs out of the drug holding means and delivering them into the trays T. The drugs are put in ampoules, vials, plastic bottles, kits, bags, or other such containers, and stored in the drug holding means in advance. The pickup means is constituted by a robot arm or the like. The pickup means picks up a drug and delivers it to a tray T at a command from the device controller 5, based on individual patient identification information, prescription information, or the like.

The card processing unit 10 is disposed opposite the tray transport path P (transportation unit) and downstream from the drug delivery unit 3. The card processing unit 10 takes out an unprinted rewritable card RC from a tray T, and automatically attaches a printed rewritable card RC to the tray T. The card processing unit 10 has a handling mechanism (card attachment unit) 20, a card conveyance mechanism (card supply unit) 30, a card position correcting mechanism 40, a card printing mechanism (card preparation unit) 50, and a card holder (card supply unit (card holding unit)) 70. The configuration of the card processing unit 10 will be discussed in detail below.

Figure 7:
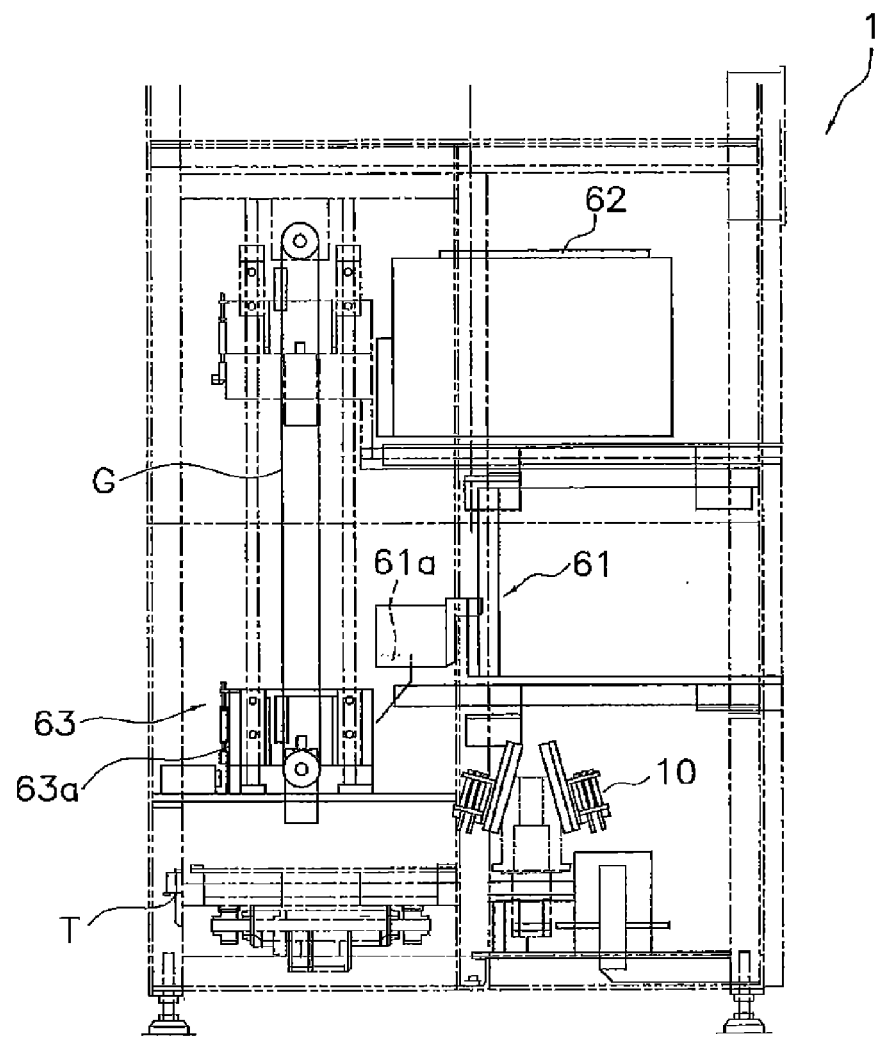
FIG. 7 is a see-through side view of the drug delivery device pertaining to this embodiment.

As shown in FIG. 7, the label/prescription printing unit 6 is disposed above the card processing unit 10. The label/prescription printing unit 6 normally prints out a drug administration label and a prescription. The label/prescription printing unit 6 also selectively prints out a tray label, which is a substitute for a card RC in a case where an error occurred in the card processing unit 10. The label/prescription printing unit 6 then inserts the tray label into the tray T. Just as with the rewritable card RC, what is mainly printed on the tray label is patient identification information. The drug administration label is printed not only with patient identification information, but also with drug administration information. If the tray label and the drug administration label are both printed, they may be printed on a single piece of paper that can be divided, or they may be printed on separate pieces of paper.

The completed tray stacking unit 7 stacks and holds trays T to which drugs, printed rewritable cards RC (or tray labels), drug administration labels, prescriptions, and so forth have been provided. The stacked trays T are transported by cart. The drugs in the trays T transported by cart go through drug inspection before being handed over to patients.

The drug delivery device 1 further comprises the device controller 5 (FIG. 8) and the managing device 310 that function as controllers.

The device controller 5 is a computer that controls the drug delivery device 1, and performs control of the tray supply unit 2, the drug delivery unit 3, the tray transport path P, the label/prescription printing unit 6, the completed tray stacking unit 7, the card processing unit 10, and so forth.

The managing device 310 is also a computer that controls the drug delivery device 1, and receives patient identification information, drug administration information, prescription information, and so forth from the electronic chart system 300, and issues commands to print rewritable cards RC, tray labels, drug administration labels, and prescriptions, and commands to supply rewritable cards RC, on the basis of the above information, a request from the device controller 5, etc.

The drug delivery device 1 pertaining to this embodiment will now be described while focusing on the structures of the respective mechanisms and the control of the card processing unit 10, which are the characteristic components of the present invention.

1.2. Card Processing Unit 10

FIG. 2 is a schematic view of the card processing unit 10. The card processing unit 10 prints patient identification information on unprinted rewritable cards RC, and automatically attaches printed rewritable cards RC to trays T filled with drugs. The card processing unit 10 provides a means for more reliably attaching and removing rewritable cards RC to and from the trays T, and reducing as much as possible the time during which the trays T are stopped.

The card processing unit 10 has a handling mechanism 20, a card conveyance mechanism 30, a card position correcting mechanism 40, a card printing mechanism 50, and a card holder 70.

The handling mechanism 20 is disposed opposite the tray transport path P. The handling mechanism 20 takes out an unprinted rewritable card RC held in the card pocket 4 of a tray T, and attach a printed rewritable card RC held by the card conveyance mechanism 30 to the tray T.

The card conveyance mechanism 30 is disposed to the rear of the handling mechanism 20. The card conveyance mechanism 30 holds rewritable cards RC, turns them face up or down as necessary, and inserts or removes rewritable cards RC into or from the card printing mechanism 50.

As shown in FIG. 2, the card position correcting mechanism 40 is disposed in an L shape with respect to the handling mechanism 20. The card position correcting mechanism 40 performs planar positioning of the rewritable cards RC so as to sandwich both sides and the corners of the rewritable cards RC that have been placed substantially horizontally.

The card printing mechanism 50 is disposed contiguously with the card position correcting mechanism 40, and along with the card position correcting mechanism 40, forms the conveyance path of the rewritable cards RC that is parallel to the tray transport path P. The card printing mechanism 50 prints the patient identification information on the unprinted rewritable cards RC to prepare printed rewritable cards RC to be attached to the trays T.

The card holder 70 is disposed right after the card printing mechanism 50, and along with the card position correcting mechanism 40 and the card printing mechanism 50, forms the conveyance path of the rewritable cards RC that is parallel to the tray transport path P. The card holder 70 stocks plural unprinted rewritable cards RC, and supplies unprinted rewritable cards RC to the card printing mechanism 50 as needed. In particular, the card holder 70 supplies an unprinted rewritable card RC (first card), which is attached to a tray T1 (first conveyance receptacle) that is first transported after the drug delivery device 1 gets started running. The card holder 70 also supplies an unprinted rewritable card RC (second card) to be attached to a tray T2 transported next when the device could not or failed to obtain an unprinted rewritable card RC (second card) from the tray T1 or a tray T2 (second conveyance receptacle) that is transported after the tray T1. The respective mechanisms of the card processing unit 10 will be described below in detail.

1.2.1. Handling Mechanism 20

Figure 4:
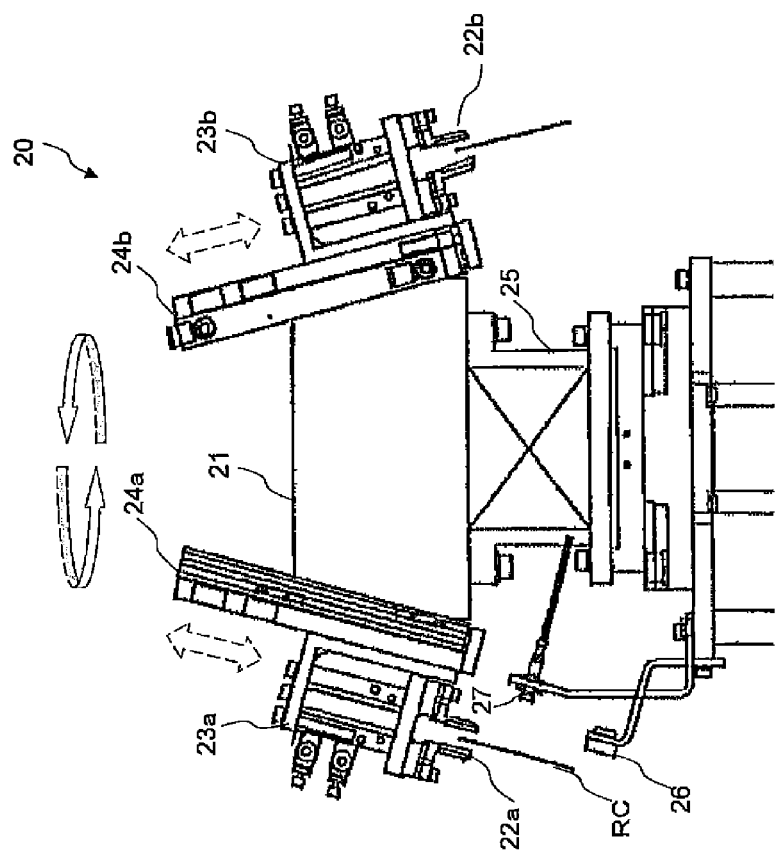
FIG. 4 is a front view of the handling mechanism pertaining to this embodiment.

As shown in FIG. 4, the handling mechanism 20 has an arm 21, a pair of card grippers 22a and 22b, a pair of supports 23a and 23b, a pair of guides 24a and 24b, a vertical rotation shaft 25, a first card sensor (card detector) 26, and a third card sensor 27.

The arm 21 is supported at its middle by the vertical rotation shaft 25, and the card grippers 22a and 22b are formed at the two ends of the arm.

The card grippers 22a and 22b are provided to the ends of the arm 21 so as to be able to clamp the edges of rewritable cards RC. The card grippers 22a and 22b are also formed so as to be inclined toward the vertical rotation shaft 25, matching the angle of the card pocket 4 of the tray T.

The supports 23a and 23b support the card grippers 22a and 22b, and as shown by the arrows in FIG. 4, are formed so as to be able to move up and down along the guides 24a and 24b together with the card grippers 22a and 22b. The supports 23a and 23b are also formed so as to be inclined toward the vertical rotation shaft 25, just as are the card grippers 22a and 22b.

The guides 24a and 24b support the supports 23a and 23b on the arm 21. The guides 24a and 24b are also formed so as to be inclined toward the vertical rotation shaft 25, just as are the card grippers 22a and 22b and the supports 23a and 23b.

The vertical rotation shaft 25 supports the center of the arm 21 and has an axis that is substantially perpendicular to the plane on which the device is installed. As shown by the arrows in FIG. 4, the vertical rotation shaft 25 is formed so as to be able to rotate around this axis.

The first card sensor 26 is provided so as to be opposite the transport path P. The first card sensor 26 is, for example, an optoelectric sensor having a light projecting and receiving element. The first card sensor 26 mainly checks for the presence of a rewritable card RC in the card pocket 4. The first card sensor 26 detects a rewritable card RC, for example, in the card pocket 4. The first card sensor 26 can detect, for example, that there is no unprinted rewritable card RC in the card pocket 4, that the card grippers 22a and 22b have missed gripping an unprinted rewritable card RC in the card pocket 4 and dropped it, that a printed rewritable card RC has fallen before being inserted into the card pocket 4, or the like. The third card sensor 27 can detect that the card grippers 22a and 22b have missed gripping an unprinted rewritable card RC in the card pocket 4 and dropped it. The first and third card sensors 26 and 27 send an error signal to the device controller 5 if a rewritable card RC cannot be sensed. The device controller 5 responds to this error signal by issuing a request to the managing device 310 to print a tray label, or issuing a request to supply an unprinted rewritable card RC.

The handling mechanism 20 operates as follows.

A motor or other such drive component (not shown) provides drive at a command from the device controller 5, and the supports 23a and 23b are lowered along the guides 24a and 24b. The card grippers 22a and 22b, which descend along with the supports 23a and 23b, grasp an unprinted rewritable card RC held in the card pocket 4 of the tray T, and a printed rewritable card RC held in the card conveyance mechanism 30, respectively. When the card grippers 22a and 22b have grasped the unprinted rewritable card RC and the printed rewritable card RC respectively, the supports 23a and 23b rise along the guides 24a and 24b. The vertical rotation shaft 25 then rotates 180 degrees. After this rotation, the supports 23a and 23b descend. The card gripper 22a then passes the unprinted rewritable card RC to the card conveyance mechanism 30, and the card gripper 22b inserts the printed rewritable card RC into the card pocket 4 of the tray T.

1.2.2. Card Conveyance Mechanism 30

Figure 5:
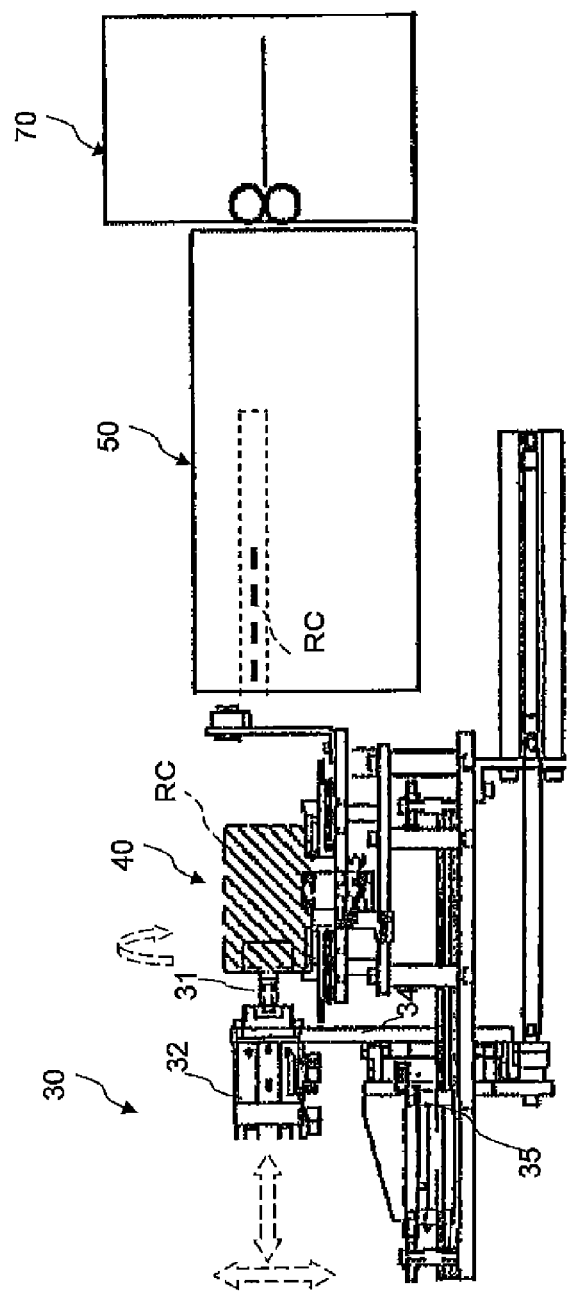
FIG. 5 is a side view of the card conveyance mechanism pertaining to this embodiment.

As shown in FIGS. 3 and 5, the card conveyance mechanism 30 has a card support 31, a support 32, a horizontal rotation shaft 33, a vertical guide 34, and a longitudinal guide 35.

The card support 31 is formed so as to be able to rotate around the horizontal rotation shaft 33, and holds a rewritable card RC.

The support 32 is formed so as to support the card support 31 above the card position correcting mechanism 40. The support 32 is also formed so as to be able to be moved back and forth by the longitudinal guide 35 and moved up and down by the vertical guide 34.

The horizontal rotation shaft 33 has an axis that is substantially parallel to the plane on which the device is installed, and is formed so as to be able to rotate around this axis.

The vertical guide 34 is formed so as to guide the support 32 in the up and down direction of FIG. 5.

The longitudinal guide 35 is formed so as to guide the support 32 in the back and forth direction of FIG. 5, that is, the backward and forward direction with respect to the card printing mechanism 50.

The card conveyance mechanism 30 operates as follows.

As shown in FIGS. 3 and 5, the card support 31 receives an unprinted rewritable card RC grasped at an angle by the card grippers 22a or 22b of the handling mechanism 20. The card support 31 rotates around the horizontal rotation shaft 33 to put the unprinted rewritable card RC in a horizontal state, and then the support 32 is lowered by the driven vertical guide 34, which places the unprinted rewritable card RC in the card position correcting mechanism 40.

Then, a second card sensor 42 (FIG. 6) of the card position correcting mechanism 40 senses the unprinted rewritable card RC. The second card sensor 42 sends a card sensed signal to the device controller 5. In response, the device controller 5 issues a command to the card conveyance mechanism 30. The device controller 5 also directs the card conveyance mechanism 30 to flip the unprinted rewritable card RC over if needed.

After this, the card support 31 lets go of the unprinted rewritable card RC, and the unprinted rewritable card RC is positioned by the card position correcting mechanism 40. The position-corrected unprinted rewritable card RC is held by the card support 31, after which the card position correcting is released.

In a state in which the card support 31 is holding the unprinted rewritable card RC horizontal, the support 32 is raised by the driven vertical guide 34. The support 32 is then advanced by the driven longitudinal guide 35 toward the card printing mechanism 50. After the card support 31 lets go of the unprinted rewritable card RC, the unprinted rewritable card RC is inserted into the card printing mechanism 50 as indicated by the imaginary lines in FIG. 5.

When the printing of a rewritable card RC is finished, the card is ejected by the card printing mechanism 50, and the card support 31 grasps the printed rewritable card RC. The support 32 is retracted by the driven longitudinal guide 35, and the printed rewritable card RC is taken out of the card printing mechanism 50.

The support 32 is then lowered by the driven vertical guide 34, and the printed rewritable card RC is placed in the card position correcting mechanism 40. The card support 31 lets go of the printed rewritable card RC, and the printed rewritable card RC is positioned by the card position correcting mechanism 40. The position-corrected printed rewritable card RC is held by the card support 31, after which the card position correcting is released.

The support 32 is then raised by the driven vertical guide 34. The card support 31 rotates around the horizontal rotation shaft 33, and the printed rewritable card RC is moved from its horizontal state to the inclined state shown in FIG. 4 and passed to the card grippers 22a and 22b of the handling mechanism 20.

The front or back direction of the printed rewritable card RC when it is passed to the handling mechanism 20, and the front or back direction of the unprinted rewritable card RC when it is inserted into the card printing mechanism 50, are determined in advance. The card conveyance mechanism 30 flips the rewritable card RC over as needed by rotation of the horizontal rotation shaft 33, on the basis of information about the predetermined front and back direction, or a signal from the second card sensor 42.

1.2.3. Card Position Correcting Mechanism 40

Figure 6:
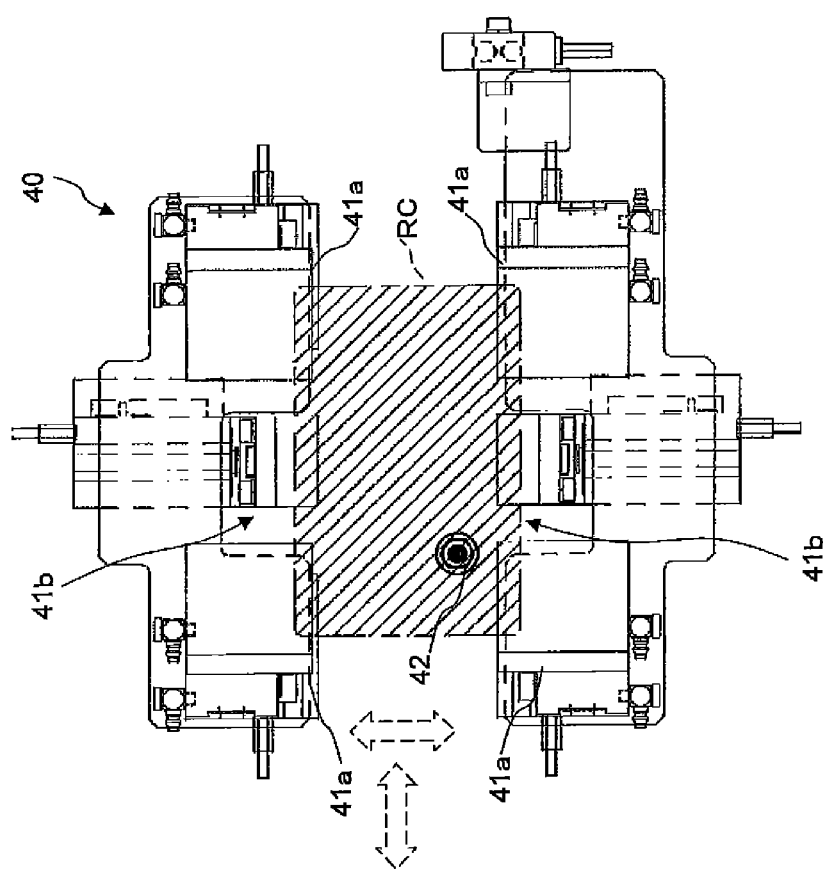
FIG. 6 is a top view of the card position correcting mechanism pertaining to this embodiment.

As shown in FIG. 6, the card position correcting mechanism 40 has first position correctors 41a, second position correctors 41b, and the second card sensor 42.

As shown by the imaginary line arrows in FIG. 6, the first position correctors 41a sandwich the corners of a rewritable card RC placed substantially in the horizontal direction, and thereby perform planar positioning of the rewritable card RC to the left and right and in the longitudinal direction. Further, the second position correctors 41b sandwich the long sides of the rewritable card RC, and thereby perform planar and lateral positioning of the rewritable card RC.

The second card sensor 42 is an optoelectric sensor having a light projecting and receiving element. For example, it is a color sensor that makes use of a three-color (red, blue, green) LED light source for a light projecting element, and that shines a spot of light on a substance and performs color discrimination by color component analysis of light received by reflection from the substance. The second card sensor 42 senses a rewritable card RC and sends a signal to the device controller 5. The device controller 5 decides from the transmitted signal whether or not a rewritable card RC is present and which way it is facing (back or front). The second card sensor 42 may also be a CCD camera, and the device controller 5 may decides whether or not a rewritable card RC is present and which way it is facing (back or front) by recognizing the obtained image.

1.2.4. Card Printing Mechanism 50

The card printing mechanism 50 produces a printed rewritable card RC by printing specific information on a rewritable card RC on the basis of patient identification information, based on a command from the device controller 5 via the managing device 310.

The card printing mechanism 50 has, for example, a hot roller, a thermal head, or another such thermal energy imparting component in its interior, and thermal energy of a specific temperature is applied to the information display face of the inserted rewritable card RC, thereby erasing or writing information from or to the information display face. Rewritable card printing devices such as this are well known, and thus will not be described in detail here.

1.2.5. Card Holder 70

The card holder 70 holds plural rewritable cards RC. The device controller 5 outputs a request to the managing device 310 to supply an unprinted rewritable card RC. According to the request, the managing device 310 issues a command to the card printing mechanism 50 to supply a rewritable card RC. In response to the request for supplying a rewritable card, the card holder 70 supplies a rewritable card RC to the card printing mechanism 50.

The card holder 70 first supplies an unprinted rewritable card RC1 to be attached to a tray T1 that is transported first after the drug delivery device 1 gets started running. The card holder 70 then supplies an unprinted rewritable card RC2 to be attached to a tray T2 transported next in a case where the device could not or failed to obtain an unprinted rewritable card RC2 from the tray T1 or a previous tray T2.

1.3. Label/Prescription Printing Unit 6

As shown in FIG. 7, the label/prescription printing unit 6 has a label printing mechanism 61 for printing tray labels and drug administration labels, a prescription printing mechanism 62 for printing prescriptions, and an insertion mechanism 63 for inserting the printed prescriptions and labels.

The label printing mechanism 61 is disposed above the card processing unit 10, and normally prints out drug administration labels listing drug administration information, but if an error occurs in the card processing unit 10, then a tray label, which displays patient identification information and takes the place of the rewritable card RC, is printed in addition to the drug administration label.

As shown in FIG. 7, the prescription printing mechanism 62 is disposed above the label printing mechanism 61. The prescription printing mechanism 62 prints out prescriptions for each tray T according to the prescription information for each patient.

The insertion mechanism 63 moves a pocket 63a up and down. The pocket 63a accepts a prescription from the prescription printing mechanism 62, accepts a drug administration label from the label printing mechanism 61, and inserts these into the tray T. The pocket 63a moves up and down according to commands from the device controller 5 upon receipt of an error signal as discussed below, accepts from the label printing mechanism 61 a tray label on which has been printed the same patient identification information as that on the rewritable card RC, and inserts this into the tray T.

1.3.1. Label Printing Mechanism 61

Normally, the label printing mechanism 61 prints a drug administration label according to a print command from the managing device 310. After printing, the drug administration label comes out of the discharge opening of the label printing mechanism 61 and is temporarily held in a label pocket 61a, after which it goes into the pocket 63a of the insertion mechanism 63. Drug administration labels are supplied to all of the trays T.

The label pocket 61a temporarily holds the drug administration label printed while the pocket 63a of the insertion mechanism 63 is accepting a prescription from the prescription printing mechanism 62.

Next, the typical operation of the card processing unit 10 when an error occurs will be described.

In addition to normally printing the drug administration label, the label printing mechanism 61 prints a tray label that is used in place of the rewritable card RC when an error occurs in the card processing unit 10. The label printing mechanism 61 in this case operates under a command from the managing device 310 to print a tray label, as discussed below. The tray label is affixed manually to the tray T during drug inspection or the like after transport of the tray T. The tray label is printed with patient identification information.

<When Error Occurs Before Printing of Drug Administration Label>

After the printing of the drug administration label and then the printing of the tray label, the two labels and come out of the discharge opening of the label printing mechanism 61 and are temporarily held in the label pocket 61a. After this, the labels are put into the pocket 63a of the insertion mechanism 63 and supplied to the tray T.

The same processing as above is also performed if the error occurs during the printing of the drug administration label.

<When Error Occurs After Printing of Drug Administration Label>

First, the drug administration label is supplied to the tray T through the same processing as above. During this time, the printing of the tray label is finished, after which this label comes out of the discharge opening of the label printing mechanism 61 and is temporarily held in the label pocket 61a. After this, the tray label is put in the pocket 63a of the insertion mechanism 63 and supplied to the tray T.

1.3.2. Prescription Printing Mechanism 62

The prescription printing mechanism 62 prints a prescription paper listing patient identification information. The printed prescription is put in the pocket 63a of the insertion mechanism 63 and inserted into the trays T of all patients.

1.3.3. Insertion Mechanism 63

The insertion mechanism 63 has a guide G that extends in the up and down direction in FIG. 7, and the pocket 63a that moves up and down along this guide G.

The pocket 63a of the insertion mechanism 63 is disposed opposite the label printing mechanism 61 and the prescription printing mechanism 62, and is moved up and down along the guide G by a motor or other such drive source. The pocket 63a accepts the labels and a prescription from the label printing mechanism 61 and the prescription printing mechanism 62, and inserts these into the tray T.

1.4. Device Controller 5 and Managing Device 310

Figure 8:
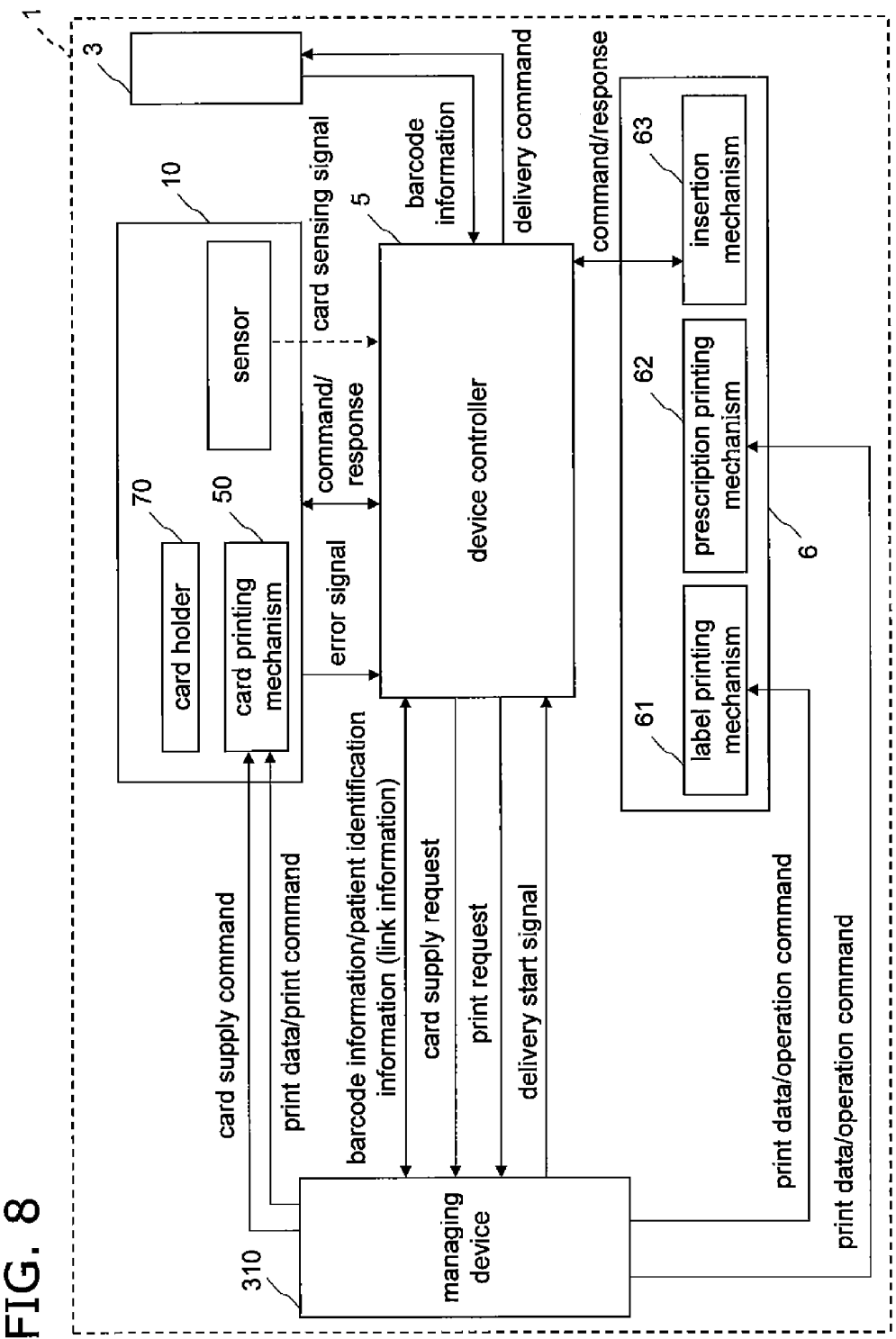
FIG. 8 is a control block diagram of the drug delivery device pertaining to this embodiment.

FIG. 8 is a control block diagram illustrating the relation between the device controller 5, the card processing unit 10, the label/prescription printing unit 6, and the managing device 310 of the drug delivery device 1.

The device controller 5 controls the operation of the various mechanisms of the label/prescription printing unit 6 and the card processing unit 10. The device controller 5 commands the operation of the label printing mechanism 61 and insertion mechanism 63 of the label/prescription printing unit 6 on the basis of specific criteria.

More specifically, the device controller 5 receives a signal that senses a rewritable card RC from sensors of the card processing unit 10 (the first card sensor 26 and third card sensor 27 of the handling mechanism 20, and the second card sensor 42 of the card position correcting mechanism 40). The device controller 5 also receives an error signal from the card processing unit 10 and sends the managing device 310 a request to print a tray label or a request to supply a rewritable card RC.

The managing device 310 receives patient identification information, drug administration information, prescription information, and the like from the electronic chart system 300 (FIG. 1), and issues commands to the drug delivery device 1 on the basis of this information.

More specifically, the managing device 310 supplies rewritable cards RC through the card printing mechanism 50 to the card holder 70 according to a request from the device controller 5 to supply rewritable cards RC. The managing device 310 outputs a command to the card printing mechanism 50 to print rewritable cards RC. The managing device 310 also outputs an operation command to the label printing mechanism 61, so that a tray label is printed, according to a request from the device controller 5 to print a tray label.

Normally, the managing device 310 outputs an operation command for printing a drug administration label to the label printing mechanism 61. The managing device 310 outputs an operation command for printing a prescription corresponding to the prescription information to the prescription printing mechanism 62.

The managing device 310 also sends and receives barcode information and patient identification information (link information) to and from the device controller 5. More specifically, the managing device 310 receives, via the device controller 5, barcode information for a tray T (tray identification information) read by a barcode reader (not shown) of the drug delivery unit 3. The managing device 310 produces link information that correlates this barcode information with drug information based on patient identification information or patient prescription information, for example, and sends this to the device controller 5. The device controller 5 stores this link information in a memory. The device controller 5 also sends a drug delivery command to the drug delivery unit 3.

According to the managing device 310, the device controller 5 of the drug delivery device 1 starts transportation of the tray T1 in response to a delivery starting signal. At the same time, the device controller 5 sends a card supply request to the managing device 310. The managing device 310 sends, to the card holder 70 via the card printing mechanism 50 of the card processing unit 10, a command for supplying a rewritable card RC1 to the card printing mechanism 50. This process of control enables the device to start printing the rewritable card RC1 beforehand and attach it to the tray T1 transported first after the start of running of the drug delivery device 1.

The device controller 5 receives a detection signal for a rewritable card RC from the first or third card sensor 26, 27 of the handling mechanism 20, or the second card sensor 42 of the card position correcting mechanism 40. If the device controller 5 does not receive the detection signal, it determines that there is no unprinted rewritable card RC. The device controller 5 then sends a request for supplying a card to the managing device 310. The managing device 310 sends, to the card holder 70 via the card printing mechanism 50 of the card processing unit 10, a command for supplying a rewritable card RC to the card printing mechanism 50. This process of control ensures a stable card supply even when the device could not or failed to obtain a new rewritable card RC from the tray T or when such similar erroneous events occurred.

1.5. Overall Flow

Figure 9A:
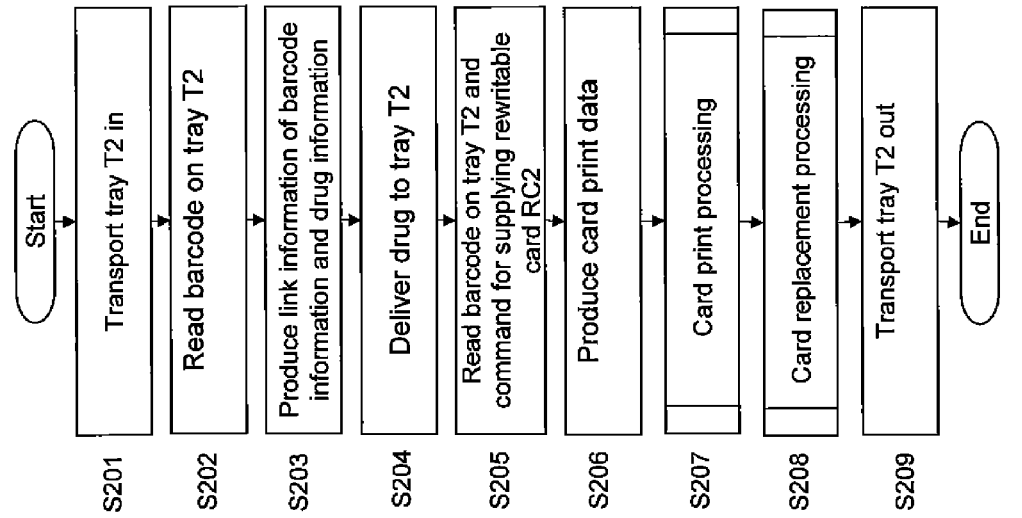
FIG. 9 is a flowchart of the overall flow of an operation of the card processing unit pertaining to this embodiment.
Figure 9B:
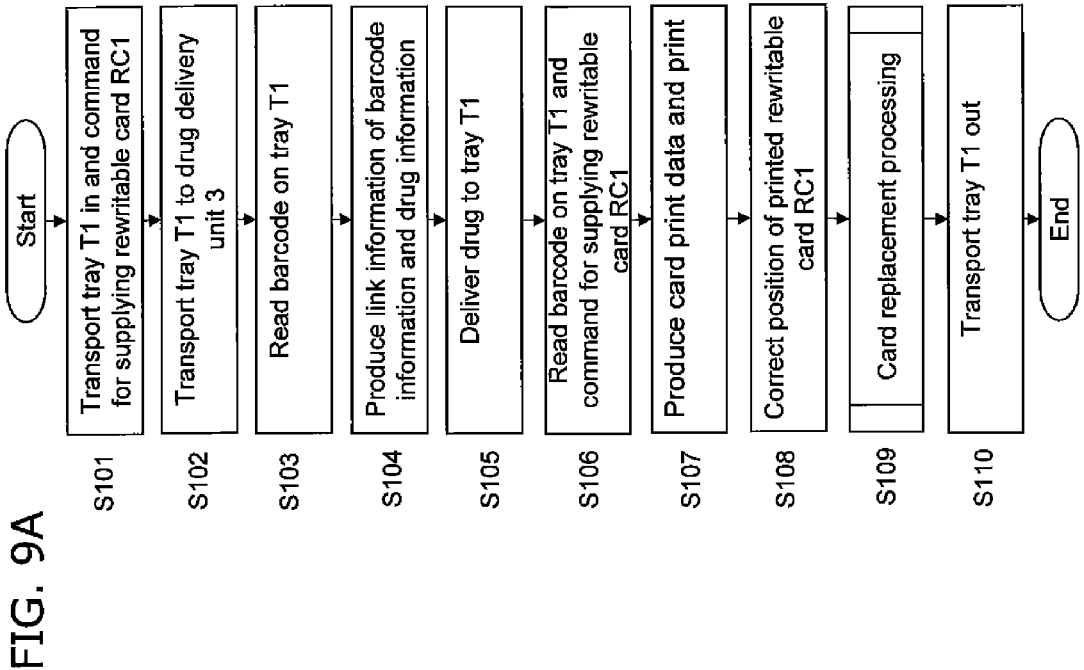

FIGS. 9A and 9B show the flows of a series of processing in which in response to a delivery starting signal from the managing device 310, a tray T1 is first transported and an unprinted rewritable card RC2 is taken out from the tray T1 and printed, and substantially at the same time, a printed rewritable card RC1 is attached to the tray T1, and then the printed rewritable card RC2 is attached to a subsequent tray T2.

In this embodiment, a rewritable card RC1 (first card) to be attached to the tray T1 (first conveyance receptacle) first transported is supplied from the card holder 70 and printed while the tray T1 is transported to the card processing unit 10. The unprinted rewritable card RC2 (second card) installed ahead of time in each tray T is printed with patient identification information corresponding to the drug delivered to one subsequent tray T (second conveyance receptacle). Accordingly, the unprinted rewritable card RC that had been installed on each tray T is taken off, and at the same time, a printed rewritable card RC on which has been printed patient identification information corresponding to the drug delivered to that tray is installed. As a result, the standby time for the tray T is shortened, and transport efficiency is improved.

To facilitate understanding, the processes for a tray T1 and a subsequent tray T2 will be described below, but it is assumed that the tray T2 may be any tray T transported after the tray T1 and all the trays are processed similarly. Also, the tray T1 and the trays T2 are sequentially transported and processed in parallel. The following processing is just one example, and the present invention is not limited to this.

The tray T1 is processed as described below and shown in FIG. 9A.

The following is premised on the production of drug information by the managing device 310 for drug delivery on the basis of a patient's prescription information.

Step S101: In response to a delivery starting signal from the managing device 310, the device controller 5 of the drug delivery device 1 starts transportation of a tray T1. At the same time, the device controller 5 sends a request for supplying a card to the managing device 310. The managing device 310 sends, to the card holder 70 via the card printing mechanism 50 of the card processing unit 10, a command for supplying a rewritable card RC1 to the card printing mechanism 50.

Step S102: The tray T1 is transported to the drug delivery unit 3 from the tray supply unit 2.

Step S103: The barcode reader (not shown) of the drug delivery unit 3 reads barcode information on the tray T1 (tray identification information) and sends it to the managing device 310.

Step S104: The managing device 310 produces link information that correlates the above-mentioned barcode information with the above-mentioned drug information, and sends this to the device controller 5 of the drug delivery device 1. The link information is stored in a memory of the device controller 5.

Step S105: Drugs are delivered sequentially to the tray T1 on the basis of the drug information for that patient.

Step S106: At the point when the immediately prior drug delivery of the card processing unit 10 is completed by the drug delivery unit 3, the barcode information of that tray T1 is read by a barcode reader 71 and sent to the managing device 310. A command for supplying a rewritable card RC1 is also issued.

Step S107: The managing device 310 produces card printing data on the basis of the patient identification information corresponding to the above-mentioned barcode information. The card printing data is outputted to the card printing mechanism 50 from the managing device 310 and printed on the rewritable card RC1.

Step S108: The printed rewritable card RC1 is taken out from the card printing mechanism 50 by the card conveyance mechanism 30. Then, the position of the printed rewritable card RC1 is corrected by the card position correcting mechanism 40 after having been released from the card conveyance mechanism 30.

Step S109: The card processing unit 10 performs card replacement processing (steps S1071 to S1078). The printed rewritable card RC1 then is attached to the tray T1.

Step S110: The tray T1 with the printed rewritable card RC1 attached thereto is transported out.

The tray T2 transported subsequent to the tray T1 is processed as described below and shown in FIG. 9B.

Step S201: The tray T2 is transported to the drug delivery unit 3 from the tray supply unit 2.

Step S202: The barcode reader (not shown) of the drug delivery unit 3 reads barcode information on the tray T2 (tray identification information) and sends it to the managing device 310.

Step S203: The managing device 310 produces link information that correlates the above-mentioned barcode information (tray identification information). with the above-mentioned drug information, and sends this to the device controller 5 of the drug delivery device 1. The link information is stored in a memory of the device controller 5.

Step S204: Drugs are delivered sequentially to the tray T2 on the basis of the drug information for that patient.

Step S205: At the point when the immediately prior drug delivery of the card processing unit 10 is completed by the drug delivery unit 3, the barcode information of that tray T2 is read by a barcode reader 71 and sent to the managing device 310. At the same time, a command for supplying a rewritable card RC2 is also issued.

Step S206: The managing device 310 produces card printing data on the basis of the patient identification information corresponding to the above-mentioned barcode information.

Step S207: Card print processing of the rewritable card RC2 to be attached to the tray T2 is performed by the card processing unit 10 (steps S1001 to S1011).

Step S208: The card processing unit 10 performs card replacement processing and attached the printed rewritable card RC2 to the tray T2. This card replacement processing is performed similarly to the card replacement processing in steps S1071 to S1078, which will be described later.

Step S209: The tray T2 with the printed rewritable card RC2 attached thereto is transported out.

1.5.1. Card Replacement Processing by Card Processing Unit 10

Figure 10:
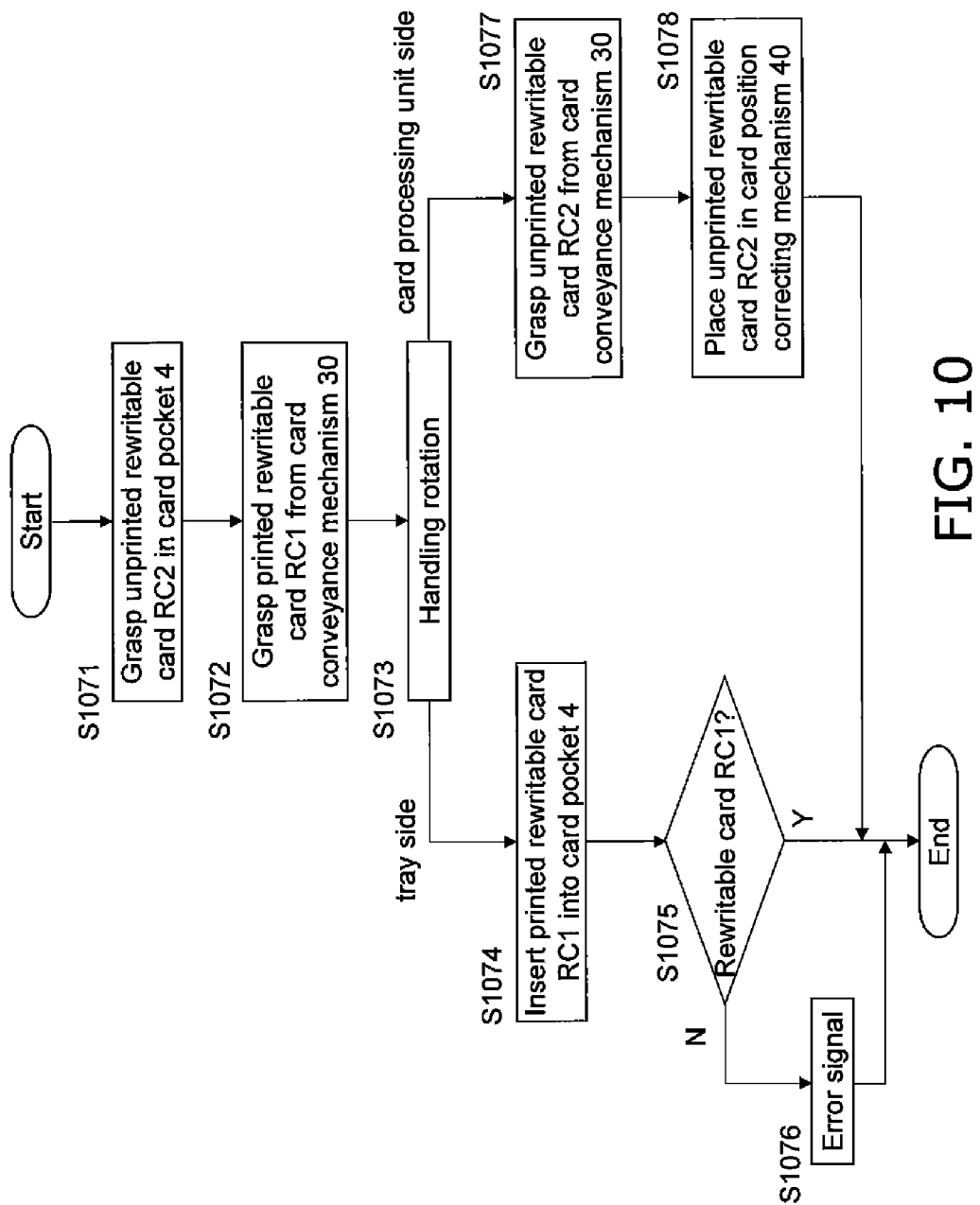
FIG. 10 is a flowchart of the card replacement processing of the card processing unit pertaining to this embodiment.

FIG. 10 shows the flow of card replacement processing by the card processing unit 10.

Step S1071: The unprinted rewritable card RC2 in the card pocket 4 of the tray T1 is grasped by the card gripper 22a of the handling mechanism 20 of the card processing unit 10.

Step S1072: At the same time, the printed rewritable card RC1 held by the card conveyance mechanism 30 is grasped by the other card gripper 22b of the handling mechanism 20.

Step S1073: The handling mechanism 20 rotates 180 degrees. The card gripper 22a moves to the card position correcting mechanism 40 side, and the card gripper 22b to the tray T1 side.

Step S1074: On the tray T1 side, the printed rewritable card RC1 is inserted by the card gripper 22b into the card pocket 4 of the tray T1.

Step S1075: The printed rewritable card RC1 is sensed by the first card sensor 26, and a signal is sent to the device controller 5. If no printed rewritable card RC1 has been sensed, the flow moves to step S1076.

Step S1076: The device controller 5 issues an error signal. The error signal is issued, for example, when the handling mechanism 20 has failed to attach the printed rewritable card RC1 to the tray T1. The device controller 5 receives the error signal and orders the label printing mechanism 61 via the managing device 310 to issue a label that is a substitute for a rewritable card RC1.

Step S1077: Meanwhile, on the card position correcting mechanism 40 side, the unprinted rewritable card RC2 is passed by the card gripper 22a to the card conveyance mechanism 30.

Step S1078: The unprinted rewritable card RC2 is placed in the card position correcting mechanism 40 by the card conveyance mechanism 30.

As for the tray T2, the same card replacement processing as described above is performed in Step S208 in FIG. 9B.

1.5.2. Card Print Processing by Card Processing Unit 10

Figure 11:
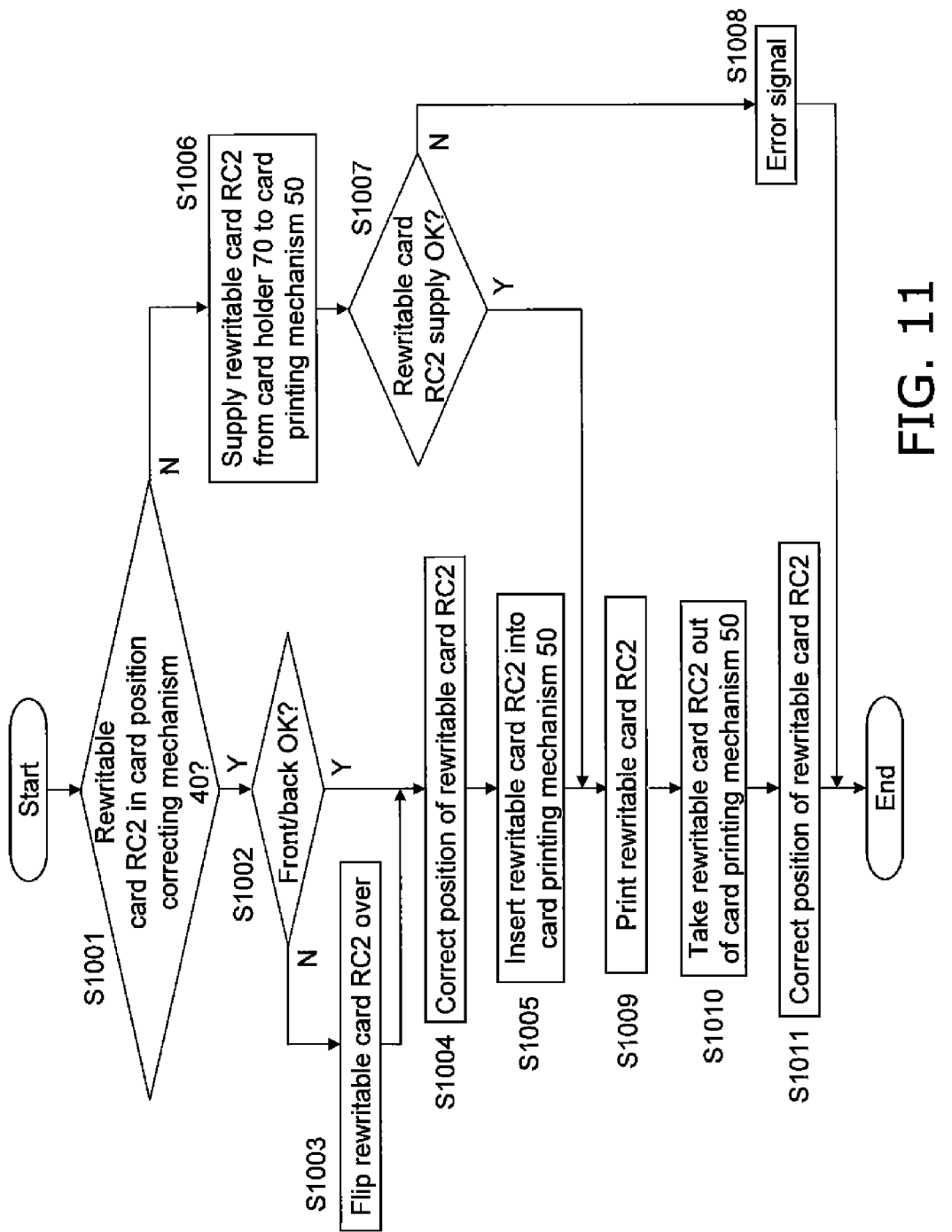
FIG. 11 is a flowchart of the card print processing of the card processing unit pertaining to this embodiment.
Figure 12:
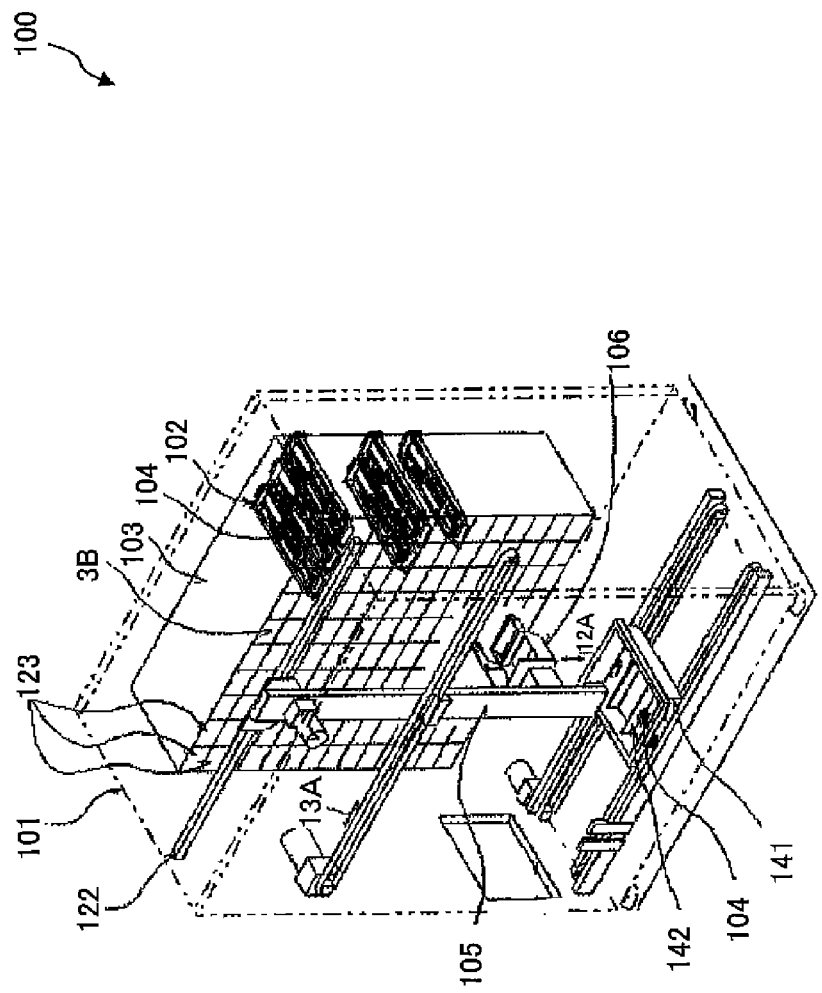
FIG. 12 is a perspective view of a conventional drug delivery device.
Figure 13:
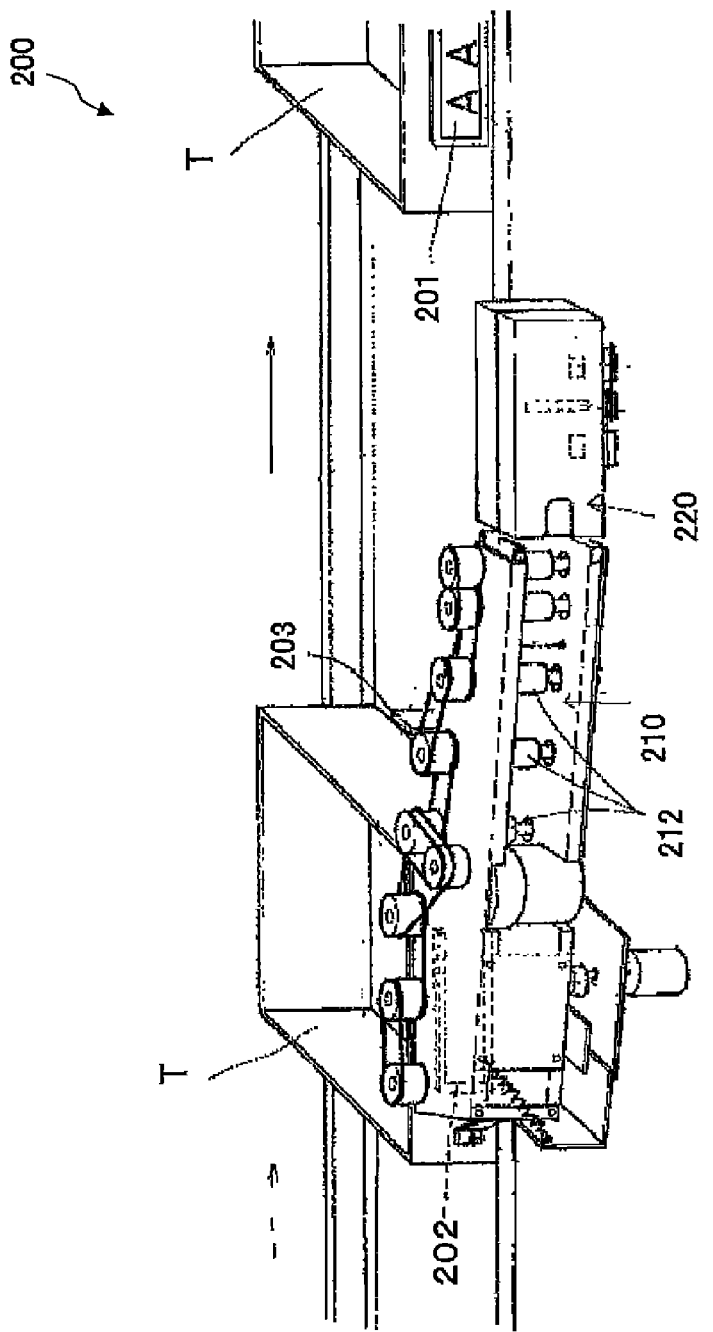
FIG. 13 is a perspective view of another conventional drug delivery device.

FIG. 11 shows the flow of card print processing by the card processing unit 10.

Step S1001: When the second card sensor 42 of the card position correcting mechanism 40 detects that a rewritable card RC2 has been placed in the card position correcting mechanism 40, a signal is sent to the device controller 5. If a rewritable card RC2 has been sensed, the flow moves to step S1002, but if no rewritable card RC2 has been sensed, the flow moves to step S1006.

Step S1002: The device controller 5 also determines from the signal of the second card sensor 42 which side of the rewritable card RC2 is the front and which is the back. If the orientation of the rewritable card RC2 is not what it is supposed to be, the flow moves to step S1003, but if it is as it is supposed to be, the flow moves to step S1004.

Step S1003: The card conveyance mechanism 30 flips over the rewritable card RC2 and puts it back in the card position correcting mechanism 40.

Step S1004: After the card conveyance mechanism 30 lets go of the rewritable card RC2, the card position correcting mechanism 40 corrects the position of the rewritable card RC2.

Step S1005: The card conveyance mechanism 30 grasps the position-corrected unprinted rewritable card RC2 and inserts it into the card printing mechanism 50.

Step S1006: On the other hand, if no rewritable card RC2 has been sensed by the second card sensor 42, the device controller 5 outputs a request to the managing device 310 to supply a rewritable card RC. The managing device 310 outputs a command to the card printing mechanism 50 to supply a rewritable card RC in response to this request. The card holder 70 supplies an extra rewritable card RC to the card printing mechanism 50 in response to this command.

Step S1007: If no extra rewritable card RC2 could be supplied from the card holder 70, the flow moves to step S1008, but if the extra rewritable card RC2 was supplied, the flow moves to step S1009.

Step S1008. The card processing unit 10 sends an error signal to the device controller 5. The error signal is issued, for example, when no rewritable card RC is supplied from the card holder 70. The device controller 5 receives the error signal and orders the label printing mechanism 61 via the managing device 310 to issue a tray label that is a substitute for a rewritable card RC2.

Step S1009: Card printing data produced by the managing device 310 is printed on the rewritable card RC2 by the card printing mechanism 50.

Step S1010: The card conveyance mechanism 30 removes the printed rewritable card RC2 from the card printing mechanism 50.

Step S1011: After the card conveyance mechanism 30 has let go of the printed rewritable card RC2, the card position correcting mechanism 40 corrects the position of the printed rewritable card RC2. After this, the printed rewritable card RC2 is passed to the handling mechanism 20 by the card conveyance mechanism 30 (the flow then goes to step S1072 of FIG. 10).

1.6. Features of this Embodiment

With the drug delivery device 1 pertaining to this embodiment, a rewritable card RC1 to be attached to a tray T1 first transported is printed with necessary information and thus prepared before the tray T1 is transported. Therefore, it is possible to attach the rewritable card RC1 to the tray T1 efficiently. Furthermore, with respect to a subsequent tray T2, a rewritable card RC2 is prepared in advance by being taken out from the tray T1 and printed with necessary information. Thus, the rewritable card RC2 can be prepared before the tray T2 is transported, so it can be attached to the tray T2 efficiently. Similarly, with respect to any of the trays T2 that include the third and its subsequent ones, a rewritable card RC2 that has been obtained from a previously transported tray T2 can be attached efficiently. As a result, the waiting time of trays during attachment of rewritable cards RC is reduced and the efficiency of transporting trays is enhanced. Thus, drug delivery efficiency can be improved.

With the drug delivery device 1 pertaining to this embodiment, a rewritable card RC1 is attached to a tray T1 first transported, and substantially at the same time, a rewritable card RC2 is taken out from the tray T1 and printed. Similarly, the printed rewritable card RC2 is attached to a tray T2 subsequent to the tray T1, and substantially at the same time, another rewritable card RC2 that is a next card is taken out from the tray T2, printed, and then attached to a further subsequent tray T2. Consequently, it is possible to obtain a rewritable card RC efficiently and reliably.

With the drug delivery device 1 pertaining to this embodiment, the card holder 70 holding plural cards is provided for supplying new rewritable cards RC. Accordingly, the rewritable card RC1 can be prepared ahead of time with respect to the tray T1 first transported, thus reducing the waiting time of tray T1. Further, in such an abnormal case that a new rewritable card RC2 can not be obtained, the card holder 70 can supply a rewritable card RC2. Since a backup supply source for new cards is provided, a shortage of cards can be prevented.

With the drug delivery device 1 pertaining to this embodiment, since the rewritable card RC is a rewritable card, once a printed rewritable card RC is inserted into the card pocket 4 of the tray T, it can still be used as an unprinted rewritable card RC for the next delivery.

2. Other Embodiments

2.1. Supply of Rewritable Cards RC

In the above embodiment, the rewritable card RC1 to be attached to the tray T1 first transported is supplied from the card holder 70, but this invention is not limited to this. The rewritable card RC1 may be set in advance, for example, in the handling mechanism 20, the card conveyance mechanism 30 or the card position correcting mechanism 40 and supplied from these mechanisms.

2.2. Attachment of Rewritable Cards RC

In the above embodiment, a rewritable card RC2 is attached to a tray T2 which is transported subsequent to a previous tray T2 from which the rewritable card RC2 has been obtained. Alternatively, a rewritable card RC2 may be attached to a tray T2 transported subsequent to the previous second tray T2, or may be attached to any tray T2 transported as a further subsequent one. Thus, when a rewritable card RC2 is to be attached after being taken can be determined flexibly in accordance with a process time taken by the card printing mechanism 50 or a transportation speed of the trays T.

2.3. Controller

In the above embodiment, the device controller 5 and the managing device 310 were provided as controllers, but the present invention is not limited to this mode. All or part of the control of each may be performed by another device, or a single device may be provided, either integrally or as a separate unit, and handle all of the control.

2.4. Card Sensor

The position of the first card sensor 26 and the third card sensor 27 of the handling mechanism 20 of the card processing unit 10, and the position of the second card sensor 42 of the card position correcting mechanism 40 are not limited to those in the above embodiment.

Also, the number of card sensors may be just one, or may be three or more. Also, the device controller 5 may decide whether or not there is an unprinted rewritable card RC or a printed rewritable card RC on the basis of signals from a plurality of card sensors at different locations.

Industrial Applicability

The present invention is useful as a drug delivery device and a drug delivery method because it has the effect of reducing a waiting time of conveyance receptacles and thus improving the drug delivery efficiency.

EXPLANATION OF REFERENCE 1 drug delivery device
2 tray supply unit
3 drug delivery unit
4 card pocket
5 device controller
6 label/prescription printing unit
61 label printing mechanism
61a label pocket
62 prescription printing mechanism
63 insertion mechanism
63a pocket
7 completed tray stacking unit
10 card processing unit
20 handling mechanism (card attachment unit)
21 arm
22a, 22b card gripper
23a, 23b support
24a, 24b guide
25 vertical rotation shaft
26 first card sensor
27 third card sensor
30 card conveyance mechanism
31 card support
32 support
33 horizontal rotation shaft
34 vertical guide
35 longitudinal guide
40 card position correcting mechanism
41a first position corrector
41b second position corrector
42 second card sensor
50 card printing mechanism (card preparation unit)
70 card holder (card supply unit (card holding unit))
71 barcode reader
300 electronic chart system
310 managing device (controller)
G guide (for insertion mechanism 63)
P tray transport path (transportation unit)
RC card (rewritable card)
RC1 card (first card)
RC2 card (second card)
T tray (conveyance receptacle)
T1 tray (first conveyance receptacle)
T2 tray (second conveyance receptacle)

What is claimed:

1. A drug delivery device that delivers a stored drug to a conveyance receptacle adapted to be attached with a card that displays desired information, said drug delivery device comprising:
   a transportation unit configured to transport plural conveyance receptacles in a sequential manner;
   a card preparation unit configured to prepare a card so as to display patient identification information thereon;
   a handling mechanism configured to remove and attach a card from and to each of the plural conveyance receptacles; and
   a sensor configured to detect a card attached to each of the plural conveyance receptacles during transportation,
   wherein when the sensor detects a card attached to a first one of the plural conveyance receptacles, the handling mechanism (i) removes the detected card from the first one of the plural conveyance receptacles, (ii) conveys the detected card to the card preparation unit, (iii) obtains the detected card that is prepared by the card preparation unit and (iv) attaches the detected card obtained from the card preparation unit to a second one of the plural conveyance receptacles that is transported after the first one of the plural conveyance receptacles, and
   when the sensor detects no card attached to the first one of the plural conveyance receptacles, the card preparation unit obtains an extra card that is preliminarily stored and prepares the extra card, and the handling mechanism obtains the extra card from the card preparation unit and attaches the extra card to the second one of the plural conveyance receptacles.

2. The drug delivery device according to claim 1, wherein while the handling mechanism attaches the detected card obtained from the card preparation unit to the second one of the plural conveyance receptacles, the handling mechanism conveys a card removed from the second one of the plural conveyance receptacles to the card preparation unit.

3. The drug delivery device according to claim 2, wherein the card is a rewritable card.

4. The drug delivery device according to claim 1, wherein the card is a rewritable card.

5. The drug delivery device according to claim 1, further comprising:
 a card supply unit configured to supply the extra card to the card preparation unit.

6. The drug delivery device according to claim 5,
 wherein the card supply unit is a card holder configured to store the extra card, and
 the card preparation unit obtains the extra card from the card holder.

7. The drug delivery device according to claim 1,
 wherein the second one of the plural conveyance receptacles is any one of the plural conveyance receptacles that is transported after the first one of the plural conveyance receptacles.

8. The drug delivery device according to claim 7,
 wherein the card preparation unit obtains the extra card from the card holder when the card preparation unit is not able to obtain a card from one of the plural conveyance receptacle.

9. A drug delivery method of delivering a stored drug to a conveyance receptacle adapted to be attached with a card that displays desired information, said drug delivery method comprising:
 transporting plural conveyance receptacles in a sequential manner;
 preparing a card so as to display patient identification information thereon;
 removing a card from each of the plural conveyance receptacles;
 attaching a card to each of the plural conveyance receptacles; and
 with a sensor, detecting a card attached to each of the plural conveyance receptacles during transportation,
 wherein when a card attached to a first one of the plural conveyance receptacles is detected, (i) the detected card is removed from the first one of the plural conveyance receptacles, (ii) the detected card is conveyed, (iii) the detected card is prepared in the preparing a card, and then (iv) the detected card is attached to a second one of the plural conveyance receptacles that is transported after the first one of the plural conveyance receptacles, and
 when no card attached to the first one of the plural conveyance receptacles is detected, an extra card that is preliminarily stored is obtained, the extra card is prepared in the preparing a card, and then the prepared extra card is attached to the second one of the plural conveyance receptacles.

* * * * *